United States Patent [19]

Naito et al.

[11] Patent Number: 4,493,752

[45] Date of Patent: Jan. 15, 1985

[54] PROCESS FOR RECOVERING TRIOXANE BY PLURAL DISTILLATION

[75] Inventors: Takeshi Naito; Junzo Masamoto, both of Kurashiki; Toshiyuki Iwaisako, Fuji; Kazuhiko Matsuzaki, Kurashiki, all of Japan

[73] Assignee: Asahi Kasei Kogyo Kabushiki Kaisha, Tokyo, Japan

[21] Appl. No.: 371,461

[22] Filed: Apr. 23, 1982

[30] Foreign Application Priority Data

Apr. 27, 1981 [JP] Japan ..................... 56-62406

[51] Int. Cl.³ .................. B01D 3/14; C07D 323/06
[52] U.S. Cl. ............................ 203/71; 203/17; 525/410; 528/492; 549/368
[58] Field of Search ............ 549/368; 564/497, 463; 203/14, 17, 71, 73, 80; 525/398, 410, 472; 528/241, 492, 501

[56] References Cited

U.S. PATENT DOCUMENTS

| | | | |
|---|---|---|---|
| 2,347,447 | 4/1944 | Walker | 549/368 |
| 3,197,437 | 7/1965 | Wall | 549/368 |
| 3,313,713 | 4/1967 | Martin | 549/368 |
| 3,378,468 | 4/1968 | Langecker | 549/368 |
| 3,433,788 | 3/1969 | Somekh et al. | 203/14 |
| 3,505,292 | 4/1970 | Smith et al. | 525/410 |
| 3,519,650 | 7/1970 | Flack et al. | 549/368 |

FOREIGN PATENT DOCUMENTS

| | | | |
|---|---|---|---|
| 590713 | 7/1947 | United Kingdom | 203/14 |
| 1027563 | 4/1966 | United Kingdom | 549/368 |

*Primary Examiner*—Wilbur Bascomb
*Attorney, Agent, or Firm*—Wyatt, Gerber, Shoup, Scobey, and Badie

[57] ABSTRACT

A process for recovering trioxane from an aqueous solution containing trioxane and triethylamine by the distillation separation process which comprises feeding an aqueous solution containing trioxane and triethylamine to the first distillation column, distilling out triethylamine, trioxane and water from the column top of the first distillation column, withdrawing an aqueous solution containing the major part of the trioxane present in the fed solution from the column bottom of the first distillation column, feeding the withdrawn solution to the second distillation column and taking out the substantially whole quantity of the trioxane fed to the second distillation column from the column top of the second distillation column.

6 Claims, 1 Drawing Figure

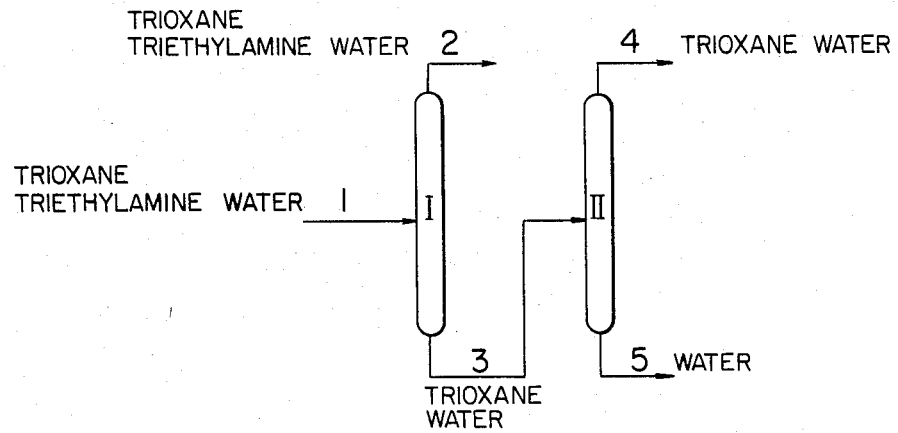

PROCESS FOR RECOVERING TRIOXANE BY PLURAL DISTILLATION

This invention relates to a process for recovering trioxane. More particularly, it relates to a process for recovering a component rich in trioxane and containing water from an aqueous solution containing trioxane and triethylamine by separating the trioxane from the triethylamine.

When trioxane is copolymerized with ethylene oxide in the presence of an acid catalyst, a polyoxymethylene copolymer is obtained. This polymer is called "polyacetal resin" which is very useful industrially. In this copolymerization reaction, it is conventional to add a base at the end point of the reaction in order to stop the reaction by neutralizing the acid catalyst. For this purpose, an aliphatic amine such as n-butylamine, triethylamine, tributylamine or the like is usually employed in an organic solvent such as benzene (Japanese Patent Publication Nos. 16,159/68 and 11,357/73).

However, nothing is known at all about the process for separating and recovering the unreacted trioxane from the solvent-amine-unreacted trioxane system resulting from neutralizing the polymerization catalyst with aliphatic amine and then washing and filtering the polymer. In Japanese Patent Publication No. 11,357/73, the recovery of three components, n-butylamine, benzene and trioxane, by distillation is mentioned. However, primary aliphatic amine such as n-butylamine forms a condensation product with the formaldehyde formed by the decomposition of trioxane, so that the process of recovery is complicated.

Further, the use of organic solvent is undesirable industrially because its combustibility restricts its handlings.

Considering the above-mentioned problems, the present inventors studied a process in which a low-boiling amine was used as the neutralizing agent for acid catalyst after the polymerization and water was used as the medium. As the result, it was found that neutralization of the polymerization catalyst with triethylamine-water system is desirable. However, triethylamine is a liquid having a boiling point of 89° C. and the trioxane separated from polymer forms a 70:30 azeotropic mixture with water at 91° C., as are well known.

In order to separate triethylamine having a boiling point of 89° C. from the azeotropic trioxane-water mixture having a boiling point of 91° C., it is necessary to use so great a plate number as economically impractical in the conventional distillations, so that such a separation process has been impossible to practice industrially.

In the separation of such a system, the basicity of triethylamine is watched in general. Thus, a method of neutralizing the triethylamine with acid at the time of distillation for the sake of lowering the volatility of triethylamine is generally thought about. However, actual study has revealed that such a process is still impossible to practice effectively practically. For example, weak acids such as acetic acid are low in the effect of lowering the volatility. Though strong acids such as sulfuric acid can lower the volatility, trioxane is decomposed by them to yield formaldehyde and therefore the object cannot be achieved. As above, there has been known no process for separating, by distillation, triethylamine and trioxane from a system consisting of triethylamine, trioxane and water.

The present inventors have conducted elaborated studies on the separation by distillation to find that trioxane and triethylamine can be separated by distillation by a process characterized by, in recovering trioxane by distillation from an aqueous solution containing trioxane and triethylamine obtainable by neutralizing the catalyst with aqueous triethylamine solution and washing trioxane-ethylene oxide copolymer with the same solution, feeding the aqueous solution containing trioxane and triethylamine to the first distillation column, distilling out the major part of the triethylamine, a part of the trioxane and water from the column top, withdrawing the aqueous solution containing the major part of the trioxane present in the fed solution from the column bottom, feeding the withdrawn aqueous solution to the second distillation column, and taking out, from column top of the second column, the substantially whole quantity of the trioxane fed to the second column. Based on this finding, the present invention has been accomplished.

The aqueous solution containing trioxane and triethylamine, used in this invention, is usually obtained by the reaction-stopping treatment in the polymerization of trioxane. Thus, just after copolymerizing trioxane and ethylene oxide as monomers by using boron trifluoride as a catalyst, the polymer is dipped into an aqueous triethylamine solution for the purpose of inactivating the catalyst and then it is filtered. The filtrate contains the unreacted trioxane, the triethylamine and a part of the catalyst. When conversion of trioxane has not reached 100%, the trioxane must be recovered.

Though the concentration of trioxane in the aqueous solution varies with polymerization conditions and concentration and amount of inactivating solution, it is usually in the range of 0.1–20% by weight and preferably in the range of 1–20% by weight. Similarly, the concentration of triethylamine also varies with the above-mentioned conditions, and it is usually in the range of 0.01–2% by weight and preferably in the range of 0.05–2% by weight. For the separation, distillation columns such as packed colum, sieve tray column, bubblecap tray column and the like are used.

In this invention, the concentration of triethylamine distilled out of column top of the first column is an important factor. When it is higher, a larger amount of triethylamine is contained in the distillate from the second column. When it is lower, the recovery rate of trioxane in the second column is lower. In this invention, the concentration of triethylamine distilled out of the column top of the first distillation column is preferably in the range of 1–30% by weight. Though the method for controlling said concentration may be dependent on the composition of the fed solution, it can be controlled by usual means such as monitoring the reflux ratio, monitoring the heat-supply condition into reboiler, monitoring the amount of distillate, or the like, so far as the composition of fed solution is constant.

The distillate of the first column thus obtained contains the major part of the triethylamine present in the starting solution and also contains trioxane. It can be reused as an inactivating agent for polymerization catalyst. Concretely, a solution prepared by diluting, with water, the aqueous solution containing triethylamine obtained from the top of the first distillation column is used for this purpose.

Next, the aqueous solution of trioxane obtained from the bottom of the first column is fed to the second column, where the residual triethylamine is removed from the column bottom and the substantially whole quantity of trioxane can be recovered from the column top. As above, this invention relates to a separation of trioxane-triethylamine-water ternary system. Although such a system has been considered impossible to separate from the viewpoint of gas-liquid equilibrium on the basis of usual knowledge, this invention has achieved the separation for the first time by controlling the two-step distillation in a specified range. Thus, this invention has an important industrial meaning.

A BRIEF DESCRIPTION OF THE DRAWING

The drawing attached is a flow diagram illustrating the process of this invention for recovering trioxane, wherein I is the first distillation column, 1 is its feeding plate, 2 is its column top and 3 is its column bottom; and II is the second distillation column, 4 is its column top and 5 is its column bottom.

Hereunder, the essence of this invention will be explained with reference to examples and the attached drawing.

EXAMPLE 1

Trioxane and ethylene oxide (2% by weight based on the trioxane) were copolymerized by using boron trifluoride dibutyl etherate as a catalyst. At the end of the reaction, the polymer was washed with an aqueous solution containing 0.2% of triethylamine. The filtrate contained 4% of trioxane.

This aqueous solution was fed to a bubble-cap tray column of 40 plates through the feeding plate (1) at a rate of 1 kg/hour. While keeping column top (2) at 90° C., a distillate consisting of 20% of triethylamine, 57% of trioxane and 23% of water was distilled out at a rate of 10 g/hour. On the other hand, while keeping the column bottom (3) at 100° C., an aqueous solution containing 3.5% of trioxane was withdrawn from the column bottom at a rate of 990 g/hour. The column bottom solution thus obtained was fed to a similar bubble-cap tray column of 40 plates (column (II)), where a composition consisting of 70% of trioxane and 30% of water was taken out from column top (4) kept at 91° C. at a rate of 50 g/hour and water was withdrawn from column bottom (5) at a rate of 940 g/hour. The trioxane recovered from the column top (4) was extracted with benzene. It could be reused as a raw material of polyacetal.

EXAMPLE 2

A 0.2% aqueous solution of triethylamine was prepared by diluting the distillate obtained from the top of the first column of Example 1 with water to 100 times its volume. A polymer copolymerized in the same manner as in Example 1 was washed with this solution and then filtered. The filtrate contained 4.6% of trioxane. By repeating the procedure of Example 1, this aqueous solution was fed to the first distillation column, and a distillate was taken out from the column top at a rate of 10 g/hour. The aqueous solution withdrawn from the column bottom was fed to the second distillation column, where a distillate consisting of 70% of trioxane and 30% of water was obtained from the column top. The trioxane was extracted and purified, and then reused for polymerization.

By this experiment, it was proved that the recovered triethylamine and trioxane had no problem at all in their reuse.

EXAMPLE 3

An aqueous solution containing 10% of trioxane and 0.5% of triethylamine was fed to the 20th plate of a distillation column packed with 40 plates of sieve trays at a rate of 1 kg/hour. An aqueous solution containing 10% of triethylamine and 58.5% of trioxane was taken out from the column top at a rate of 49 g/hour. The condensate at the column bottom was fed to the second column, where an aqueous solution containing 68% of trioxane was taken out of the column top at a rate of 106 g/hour. The distillate obtained from the column top contained no detectable amount of triethylamine.

EXAMPLE 4

The procedure of Example 3 was repeated, except that the fed aqueous solution contained 7.1% of trioxane and 0.5% of triethylamine. From the top of the first distillation column, an aqueous solution containing 10% of triethylamine and 58% of trioxane was obtained at a rate of 49 g/hour. From the top of the second distillation column, an aqueous solution containing 68% of trioxane was taken out at a rate of 62 g/hour. The latter aqueous solution contained no detectable amount of triethylamine.

EXAMPLES 5-10

The procedure of Example 3 was repeated, except that the fed solutions used had the compositions shown in Table 1 below. The results were as shown in the Table 1.

TABLE 1

| Example No. | Fed solution Composition (%) | | Amount of feed (g/hr) | Distillate of 1st column Composition (%) | | Amount of distillate (g/hr) | Distillate of 2nd column Composition (%) | | Amount of distillate (g/hr) |
| --- | --- | --- | --- | --- | --- | --- | --- | --- | --- |
| | TEA | TOX | | TEA | TOX | | TEA | TOX | |
| 5 | 0.05 | 1 | 1,000 | 9.8 | 62.3 | 5.0 | ND | 66.3 | 11.0 |
| 6 | 0.05 | 5 | 1,000 | 3.7 | 69.3 | 12.1 | ND | 65.9 | 62.3 |
| 7 | 0.1 | 1.5 | 1,000 | 32.0 | 45.0 | 3.1 | $t_r$ | 67.8 | 18.7 |
| 8 | 0.1 | 3.3 | 1,000 | 9.6 | 61.3 | 9.8 | ND | 68.2 | 35.5 |
| 9 | 0.5 | 5 | 1,000 | 25.9 | 57.8 | 18.4 | ND | 64.2 | 59.3 |
| 10 | 0.5 | 10 | 1,000 | 11.2 | 58.1 | 43.8 | ND | 68.1 | 99.9 |

TEA: Triethylamine.
TOX: Trioxane.
ND: Not detectable
$t_r$: Trace

COMPARATIVE EXAMPLE 1

Separation was carried out under the same conditions as in Example 10, except that the composition of the fed solution and the compositions of the distillates of the first and second distillation columns were different. The compositions were regulated by controlling the amount of distillates. The results were as follows, which demonstrate that the separation was insufficient:

Fed Solution TEA 0.5%, TOX 1.5%, Rate 1 kg/hour
First column TEA 38.3%, TOX 41%, Rate 11 g/hour
Second column TEA 0.4%, TOX 69%, Rate 14.4 g/hour.

Composition of the distillate from the top of the first column and temperatures in Examples mentioned above are as shown in Table 2 below.

TABLE 2

| Example | Composition of distillate from top of first column (%) | | Temperature (°C.) | | | |
| --- | --- | --- | --- | --- | --- | --- |
| | | | First column | | Second column | |
| | TEA | TOX | Top | Bottom | Top | Bottom |
| 1 | 20 | 57 | 90 | 100 | 91 | 101 |
| 2 | 20 | 57 | 90 | 100 | 91 | 101 |
| 3 | 10 | 58.5 | 91 | 100 | 91 | 101 |
| 4 | 10 | 58 | 91 | 100 | 91 | 101 |
| 5 | 9.8 | 62.3 | 91 | 100 | 91 | 100 |
| 6 | 3.7 | 69.3 | 91 | 100 | 91 | 101 |
| 7 | 32 | 45.0 | 81 | 100 | 91 | 101 |
| 8 | 9.6 | 61.3 | 91 | 100 | 91 | 101 |
| 9 | 25.9 | 57.8 | 83 | 100 | 91 | 101 |
| 10 | 11.2 | 58.1 | 91 | 100 | 91 | 101 |
| Comparative Ex. 1 | 38.3 | 41 | 77 | 100 | 91 | 101 |

TEA: Triethylamine
TOX: Trioxane

What is claimed is:

1. A process for recovering trioxane from an aqueous solution containing trioxane and triethylamine by distillation which comprises feeding an aqueous solution containing trioxane and triethylamine to a first distillation column of a distillation apparatus comprising a first and a second distillation column, distilling out triethylamine, trioxane and water as an overhead from the first distillation column, withdrawing an aqueous solution containing the major part of the trioxane present in the feed solution from the bottom of the first distillation column, feeding the withdrawn solution to the second distillation column and taking out substantially the whole quantity of the trioxane fed to the second distillation column from the overhead of the second distillation column and withdrawing water from the bottom thereof.

2. A process according to claim 1, wherein the concentration of trioxane in the aqueous solution fed to the first distillation column is 1-20% by weight based on the total weight.

3. A process according to claim 1, wherein the concentration of triethylamine in the aqueous solution fed to the first distillation column is 0.05-2% by weight based on the total weight.

4. A process according to claim 1, wherein the concentration of triethylamine in the distillate distilled out of the column top of the first distillation column is 1-30% by weight based on the total weight.

5. A process according to claim 1, wherein said aqueous solution containing trioxane and triethylamine is obtained when a copolymer prepared by using trioxane and ethylene oxide as monomers and boron trifluoride as a catalyst is washed with an aqueous solution of triethylamine and the catalyst is neutralized with the same triethylamine solution.

6. A process according to claim 5, wherein the aqueous solution of triethylamine is a solution prepared by diluting, with water, the aqueous solution containing triethylamine obtained from the overhead of the first distillation column.

* * * * *